United States Patent [19]

O'Neill et al.

[11] Patent Number: 4,704,405
[45] Date of Patent: Nov. 3, 1987

[54] RAPID ACTING COMBINATION OF SODIUM SULINDAC AND A BASE

[75] Inventors: Joseph L. O'Neill; Eugene J. Dehner, both of Lansdale, Pa.

[73] Assignee: Merck & Co., Inc., Rahway, N.J.

[21] Appl. No.: 900,201

[22] Filed: Aug. 25, 1986

[51] Int. Cl.$^4$ .............................................. A61K 31/19
[52] U.S. Cl. ..................................................... 514/568
[58] Field of Search ................ 514/569, 160, 161, 568

[56] References Cited

U.S. PATENT DOCUMENTS 3,654,349  4/1972  Shen et al. ..................... 260/515 M
4,402,979  9/1983  Shen et al. ........................... 514/569

FOREIGN PATENT DOCUMENTS 134672   1/1973  Fed. Rep. of Germany .
2059768  4/1981  United Kingdom .

Primary Examiner—Stanley J. Friedman
Attorney, Agent, or Firm—Theresa Y. Cheng; Micheal C. Sudol

[57] ABSTRACT

A water-soluble combination of sodium sulindac and an appropriate base, for example, tromethamine or sodium bicarbonate, has been found to exhibit unexpectedly improved onset of activity relative to conventional water-soluble formulations containing sodium sulindac.

6 Claims, No Drawings

RAPID ACTING COMBINATION OF SODIUM SULINDAC AND A BASE

BACKGROUND OF THE INVENTION

It is well known that in evaluating a drug's merit, considerations of onset (bioavailability) and adverse side effects are inseparable from the drug's efficacy. Each is an important part of the drug's overall therapeutical profile. An early onset is important. It brings the relief quickly and therefore promotes patient compliance.

Sulindac is a non-steroidal antiinflammatory and analgesic drug (NSAID) known since the early 1970's. It is claimed in U.S. Pat. No. 3,654,349 issued to T. Y. Shen et al. in April 1972, and commercialized by Merck & Co., Inc. under the tradename CLINORIL. However, sulindac has a slow onset of activity which is due to its poor solubility in an acidic environment such as the stomach.

Sulindac is insoluble in water below pH 4.5, but its sodium salt is very soluble. It was thought that sodium sulindac, like sodium salts of other NSAIDs, for example, indomethacin, should have a much better bioavailability and a much shorter onset of activity than the parent compound, sulindac itself. Surprisingly, no appreciable difference in onsets was found between sulindac tablets and the aqueous solution of sodium sulindac in spite of numerous experiments. Based on historical data in man, sodium sulindac given as an oral solution exhibited no improved onset of activity when compared to sulindac given as a tablet, 10 mg/ml or 40 mg/ml oral suspension, a rectal suppository, an intramuscular injection suspension or even as its active metabolite (sulindac sulfide).

Tromethamine or sodium salts of indomethacin, naproxen and aspirin are known (British Pat. No. 2,059,768; and German Pat. No. 134,672). These salts all showed enhanced bioavailability of the drug. Thus, it was totally unexpected that no such conventional improvement of bioavailability or onset of activity was observed for the sodium sulindac and sulindac tromethamine salt when they were tested by themselves.

Although sodium sulindac, sodium bicarbonate and tromethamine are known, there is no known combination of these salts.

However, when a sufficient amount of a base such as tromethamine and/or sodium bicarbonate is combined with sodium sulindac, an unexpected improvement of bioavailability and an earlier onset of activity resulted.

It is therefore the object of this invention to provide a novel combination of sodium sulindac and a base with an improved onset, shorter time to peak activity and enhanced bioavailability than sodium sulindac alone.

It is also the object of this invention to provide a pharmaceutical composition of the combination for the treatment of inflammation and pain.

Finally, it is the object of this invention to develop a method of treatment comprising the administration of the novel combination to patients suffering inflammation and pain.

DETAILED DESCRIPTION OF THE INVENTION

The present invention is directed to a combination of sulindac and a base which may be tromethamine or sodium bicarbonate. The base is present in an excess amount that will improve the onset, shorten the time to peak activity of sodium sulindac by solubilizing and delivering sodium sulindac from the stomach into the duodenum for effective and rapid absorption by the body system.

Sulindac is represented by the formula (A):

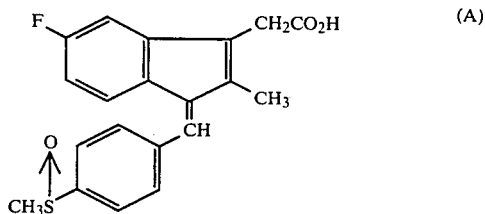

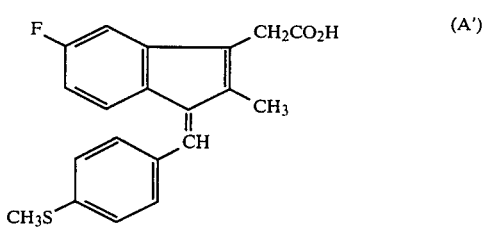

It is a NSAID with a long duration of action and is a reduction-oxidation prodrug which owe its in vivo activity to its metabolite, the active sulfide of formula (A').

Tromethamine is represented by the formula (B): $NH_2C(CH_2OH)_3$; and sodium bicarbonate is of formula: $NaHCO_3$.

The combination is used in an amount sufficient to treat inflammation and pain. Normally, the combination will contain the active ingredient, namely, sodium sulindac in an amount of from about 1 mg to 140 mg per kg body weight per day (50 mg to 10 g per patient per day), preferably from about 2 mg to 70 mg per kg body weight per day (100 mg to 5 g per patient per day), for example, the therapeutic effect is obtained from oral administration of a daily dosage of from about 200 to 500 mg/day. It should be understood, however, that although preferred dosage ranges are given, the dose level for any particular patient depends upon the age, body weight, sex, time of administration, route of administration, rate of excretion, drug combination, reaction sensitivities and severity of the particular disease of the patient.

For combinations containing sodium sulindac and tromethamine, the weight ratio is about 250 mg to 700 mg of tromethamine to about 106 mg to 636 mg of sodium sulindac. Preferably, 295 to 660 mg tromethamine is mixed with 424 mg (1.12 mEq) of sodium sulindac. It should be noted that compressed tablets containing sodium sulindac and tromethamine do not disintegrate or dissolve rapidly at simulated gastric pH's. The addition of up to 16% of the tablet weight some commonly used disintegrants or super disintegrants, e.g., acdisol and explotab, failed to effect rapid disintegration and dissolution in the presence of the commonly used lubricant magnesium stearate.

It is therefore necessary that the combination comprises, in addition to tromethamine and sodium sulindac, about 2–10% by weight of glyceryl behenate, about 2–10% by weight corn starch and about 0.1–0.5% by weight docusate sodium. The following is a representative combination of sodium sulindac and tromethamine.

|  | mg/Tablet |
|---|---|
| Sodium Sulindac | 424 |
| Tromethamine | 660 or 295 |
| Docusate Sodium | 2 |
| Corn Starch | 60 |
| Glyceryl Behenate | 70 |

For combinations containing sodium sulindac and sodium bicarbonate, the quantity of sodium bicarbonate in weight is at about 0.8 g to 2.0 g which is the amount required to neutralize the stomach and thereby allowing the discharge of sodium sulindac from the stomach to the small intestine as a solution. Extremely rapid absorption of sulindac was noted in a biliary secretion study where aqueous sodium sulindac was delivered directly to the duodenum through a triple-lumen intestinal tube.

The following is a representative combination of sodium sulindac and sodium bicarbonate:

sodium sulindac—0.212 g (equivalent to 200 mg of sulindac)
sodium bicarbonate—1.460 g Although the preferred amount of sodium sulindac is about 0.212 g it can range from 0.106 g to 0.636 g.

This invention also relates to a method of treating inflammation and pain in patients using the combination. For example, the combination of the invention can be used to treat diseases such as rheumatoid arthritis, osteoarthritis, gout, infectious arthritis and rheumatic fever. It has better bioavailability, shorter onset of activity, shorter time to peak activity than sodium sulindac alone and exhibits a lower incidence of vomiting and other adverse side effects than the parent compound.

The treatment of inflammation and pain can be accomplished by orally administering to patients a therapeutic dose of the combination, particularly in a non-toxic pharmaceutically acceptable carrier, preferably in tablet or solution form.

The non-toxic pharmaceutical carrier may be for example, either a solid or a liquid. Exemplary of solid carriers are lactose, corn starch, gelatin, talc, terotex, glyceryl behenate, terra alba, sucrose, agar, pectin, cab-o-sil, and acacia. Exemplary of liquid carriers are peanut oil, olive oil, sesame oil and water, preferably water.

The combinations may be prepared by blending sodium sulindac, a base and a suitable binding agent in a suitable mixer and granulated by addition of water or aqueous-solvent mixtures. The wet mass may be milled, dried, rescreened and blended with disintegrants and lubricants before compression. To prevent the irritancy of sulindac to the mouth and throat, the tablets may be film coated.

The following Examples illustrate the dissolution profiles of the combinations:

EXAMPLE 1

The composition for sulindac sodium with tromethamine (TRIS) contained 70 mg glyceryl behenate, 2 mg docusate sodium and 60 mg corn starch. The formulation has the following dissolution profiles (USP at 50 RPM).

| Time Minutes | % Dissolved | | | |
|---|---|---|---|---|
|  | 660 mg TRIS | | 295 mg TRIS | |
| HCl Media | 0.6 mEq | 2.45 mEq | 0.6 mEq | 2.45 mEq |
| 5 | 46 | 47 | — | — |
| 10 | 83 | 80 | 94 | 89 |
| 15 | 100 | 99 | — | — |
| 20 | 102 | 100 | 98 | 92 |
| 30 | 102 | 101 | 99 | 92 |

EXAMPLE 2

| Sulindac Sodium 424 mg Tromethamine 295 mg % Dissolved in HCl Media 2.45 mEq | | |
|---|---|---|
|  | 4% Glyceryl Behenate | |
| Time Minutes | 0.2% docusate | 5% Corn Starch 0.2% docusate |
| 10 | 8  12 | 70  89 |
| 20 | 49  80 | 97  92 |
| 30 | 88  82 | 96  92 |

What is claimed is:

1. A combination comprising (a) 0.106 to 0.639 g of sodium sulindac; and (b) 0.8 to 2.0 g of sodium bicarbonate.

2. The combination of claim 1 comprising 212 mg of sodium sulindac and 1.46 g of sodium bicarbonate.

3. A pharmaceutical composition for the treatment of inflammation and pain comprising a therapeutically sufficient amount of the combination of claim 1 and a pharmaceutically acceptable carrier.

4. The pharmaceutical composition of claim 3, comprising the combination of 212 mg of sodium sulindac; 1.46 g of sodium carbonates; and a pharmaceutically acceptable carrier.

5. A method for the treatment of inflammation and pain comprising the oral administration of a therapeutically effective amount to a patent in need of the treatment the combination of claim 1.

6. The method of claim, 5 comprising the oral administration of a therapeutically effective amount of the combination of 212 mg of sodium sulindac and 1.46 g sodium bicarbonate.

* * * * *

UNITED STATES PATENT AND TRADEMARK OFFICE
CERTIFICATE OF CORRECTION

PATENT NO. : 4,704,405

DATED : November 3, 1987

INVENTOR(S) : Joseph L. O'Neill & Eugene J. Dehner

It is certified that error appears in the above—identified patent and that said Letters Patent is hereby corrected as shown below:

Col. 4, line 47, after "1.46 g of sodium," change "carbonates;" to --bicarbonate;--.

Col. 4, line 51, after "effective amount to a," change "patent" to --patient--.

Signed and Sealed this

Nineteenth Day of April, 1988

Attest:

DONALD J. QUIGG

Attesting Officer

Commissioner of Patents and Trademarks